(12) United States Patent
Schmidt

(10) Patent No.: US 6,237,386 B1
(45) Date of Patent: May 29, 2001

(54) PROGRESSIVE WIRE FORMING SYSTEM

(75) Inventor: Philip D. Schmidt, Social Circle, GA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/476,428

(22) Filed: Dec. 30, 1999

(51) Int. Cl.$^7$ .............................. B21B 13/04; B21D 5/14
(52) U.S. Cl. ................................................. 72/232; 72/170
(58) Field of Search ........................... 72/232, 173, 174, 72/175, 170

(56) References Cited

U.S. PATENT DOCUMENTS 2,293,526 * 8/1942 Zahodiakin .......................... 72/170
4,723,431 * 2/1988 McKindary .......................... 72/170

* cited by examiner

Primary Examiner—Rodney A. Butler
(74) Attorney, Agent, or Firm—Blakely, Sokoloff, Taylor & Zafman

(57) ABSTRACT

A process for progressive wire formation is disclosed, comprising rotating a primary roller having a circumferential forming groove configured to receive a wire to be formed. A first stage roller having a circumferential forming groove configured to receive a wire to be formed engages the primary roller at a first contact point. A second stage roller having a circumferential forming groove configured to receive a wire to be formed engages the primary roller at a second contact point. A predetermined length of wire is run into the forming groove of the primary roller. The wire is compressed within the first stage roller forming groove at the first contact point and compressed within the second stage roller forming groove at the second contact point.

26 Claims, 10 Drawing Sheets

PROGRESSIVE WIRE FORMING SYSTEM

FIELD OF THE INVENTION

This invention relates to the field of wire forming fabrication methods.

BACKGROUND

For many years, wire form metal products have been a superior substitute for sheet metal or molded compositions in many applications. Wire form imparts increased strength to the article of manufacture while often reducing its weight substantially. The rounded corners and flexibility of wire form articles have found applications in the medical field as well where wire forms provide the ability to conform to irregular geometries and shapes. Such geometries and shapes can provide, for example, inner rods to hollow bore needles or to facilitate the delivery of stents in the body.

It is often desirable to have a wire with a cross-section other than round. Wires with cross-sections that are rectangular, triangular, square or some other unique geometry may be desirable. To achieve a unique cross-section in the wire, a forming process is utilized, which transforms a round wire into the desired cross-section. The forming process involves a set of rollers, where the round wire is passed between the rollers and the new geometry is pressed into the round wire. The roller set consists of a top 1 and bottom roller 2, as shown in FIG. 1, each of which have a circumferential forming groove, 3 and 4, respectively, formed into it. The groove acts as the mold or forming surface to press the round wire into the desired geometry. As a result, round wire enters the forming system, and formed wire with some other cross-sectional geometry exits the system.

Because some cross-sections may require more than one forming step in order to be transformed from round to the desired cross-section, a series of forming rollers is often utilized. The round wire is incrementally formed from round to the desired cross-section as it passes through each sequential forming station. This is because the amount of material movement that can occur in one stage of forming is limited by the material characteristics of the metal comprising the wire. Progressive forming involves the use of multiple stages which each accomplish incremental forming steps.

Currently, as shown in FIG. 2, the incremental forming process consists of individual roller sets 1, 1a and 1b arranged in a linear series, the wire 2 passing from one set to the next in each stage of the process. The wire is suspended freely between roller sets 1, 1a and 1b requiring the orientation of the wire be the same from one roller set to the next in order to fit properly within the forming grooves. Where the wire is suspended freely between roller sets, the wire spatial orientation is free to change, i.e., rotate or otherwise move out of the alignment orientation necessary to continue forming. Thus, maintaining the correct wire orientation as it passes to progressive sets of rollers can be difficult. A misfeed in the wire between roller stages, wherein the wire adopts the improper orientation and lodges within the grooves, often requires simply restarting the process anew. A more uniform method of ensuring the wire retains its correct orientation for the next forming stage would be desirable.

SUMMARY

A process for progressive wire formation is disclosed, comprising rotating a primary roller having a circumferential forming groove configured to receive a wire to be formed. A first stage roller having a circumferential forming groove configured to receive a wire to be formed engages the primary roller at a first contact point. A second stage roller having a circumferential forming groove configured to receive a wire to be formed engages the primary roller at a second contact point. A predetermined length of wire is run into the forming groove of the primary roller. The wire is compressed within the first stage roller forming groove at the first contact point and compressed within the second stage roller forming groove at the second contact point.

Other features and advantages of the invention will be apparent from the accompanying drawings and from the detailed description that follows below.

BRIEF DESCRIPTION OF THE DRAWINGS

The invention is illustrated by way of example and not by way of limitation in the figures of the accompanying drawings in which like references indicate similar elements and in which.

DETAILED DESCRIPTION

The invention provides a method of progressive forming that maintains constant control of the wire during the progressive forming process, keeping its proper orientation for successive forming in the proximate roller forming grooves. The successive linear series of roller pairs is replaced by one forming station which includes multiple rollers which maintain contact with the wire simultaneously without the wire being freely suspended between forming rollers. The invention pertains to forming wire which has applications to most any type of finished wire formed products, including those in the medical field.

Figure 1:
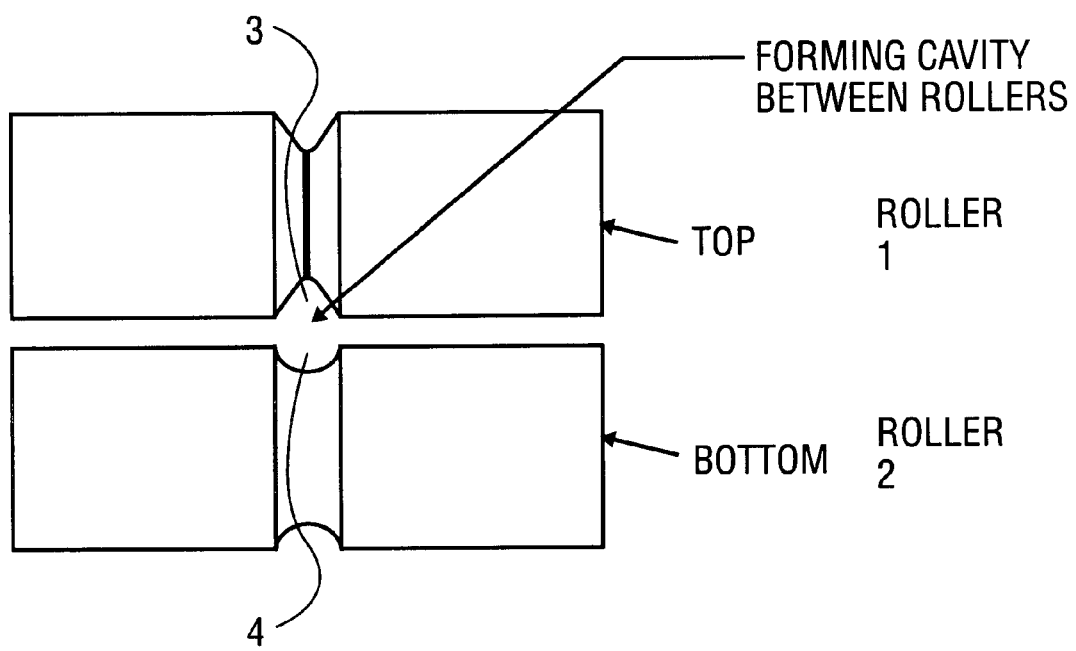
FIG. 1 shows a side view illustration of a roller set.
Figure 2:
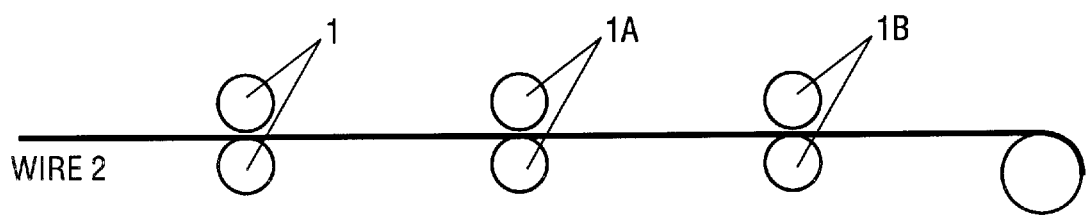
FIG. 2 illustrates the prior art method of incremental roller formation
Figure 3:
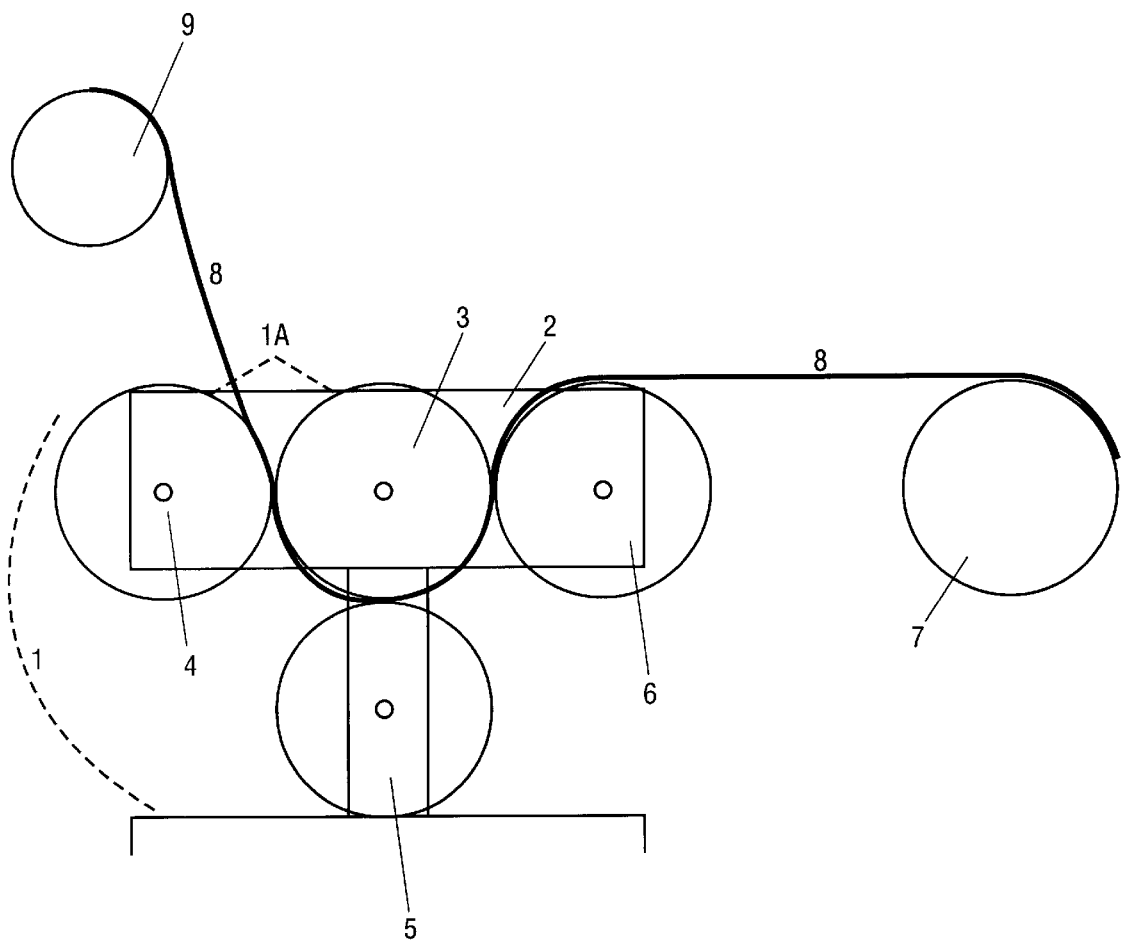
FIG. 3 illustrates the wire forming method according to one embodiment of the invention.

As shown in FIG. 3, one embodiment of the invention uses a multi-roller forming station 1 utilizing a "T" frame design 2 having a primary roller 3 at the center with progressive stage rollers 4, 5 and 6 contacting the primary roller about the primary roller circumference at both arms and at the base of "T" frame 2. In this embodiment, forming grooves (not pictured in FIG. 3, but examples of which are illustrated in FIGS. 7–10) for the wire are located on each roller, i.e., both primary and stage rollers.

The primary roller 3 is mounted in a fixed position in the center of the system. The mounting of primary roller 3 may be on a frame or other support known in the art. Each progressive roller, i.e., rollers 4, 5 and 6, is mounted on arms of "T" 2 extending outward from the center. In one embodiment the location of each progressive roller is adjustable to allow greater or lesser compressive force to be applied to the roller forming grooves to regulate the amount of forming which may occur in any one stage. In one embodiment, the primary roller rotation is driven by a drive train (not pictured). Contact with the stage rollers causes their counter rotation with respect to the driven rotation of the primary roller.

In one embodiment, during operation, a wire having a substantially round cross-section 8 enters the system from a spool 9. The wire is led into the system, passing through the first stage where it contacts the primary roller 3 and the first stage roller 4 at a point 1a. Compression by the paired rollers forms the wire which is disposed within the roller forming grooves. The wire progresses to the second stage, i.e., second stage roller 5 and primary roller 3, without losing contact with primary roller 3 and still disposed within the primary roller forming groove. The second stage involves the primary roller 3 and the second stage roller 5 which compresses the wire disposed within the roller grooves (not pictured). In the second stage, the wire continually remains within the same forming grooves of the primary roller as the first stage. Wire 8 then passes through the third, and in this embodiment, the final stage of forming. The third stage involves primary roller 3 and third stage roller 6 which compresses the wire within a forming groove of primary roller 3. The wire, formed according to the progressive compression within the forming groove of primary roller 3, is then picked up by take up spool 7.

Typically, the rollers used will be made of carbide, but can also be fashioned of hardened steel or materials with similar properties which will allow for machining or tooling to inscribe grooves or cavities for forming of a wire. Other materials will occur to those skilled in the art. In shaping wire for medical applications having a diameter of approximately 0.030", a suitable surface roller diameter is typically about three inches. It is to be appreciated that the actual size and diameter of the rollers and the shape, size and width of the forming grooves will ultimately depend on the shape and properties of wire desired and the ultimate characteristics of the wire formed article to be manufactured.

The wire to be formed in such system will have no specific metallic material limitations or requirements. The ability to form the wire and the progressive stages necessary will depend on the article to be formed. The wire used can vary widely in diameter or thickness, oftentimes it will average about 0.030 inches, variations of as much as between 0.060" and 0.010" are also easily accommodated.

Figure 6:
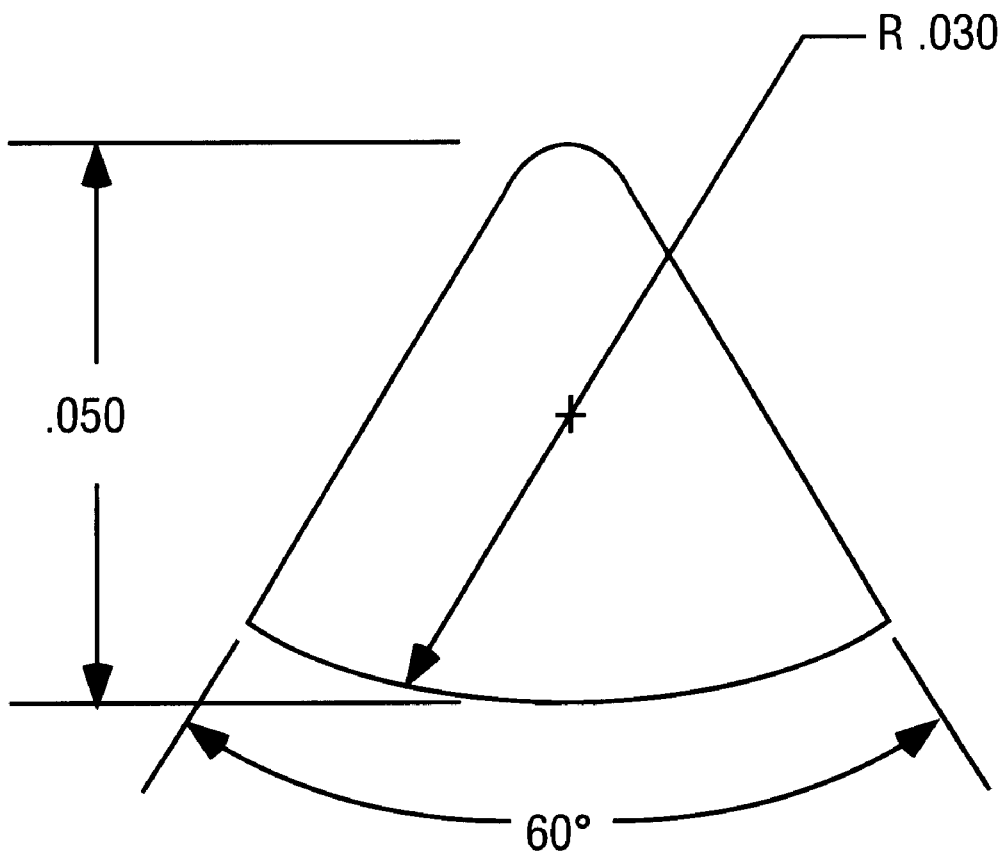
FIG. 6 is a cross-sectional view of a triangular wire to be formed using the method of the invention.
Figure 7:
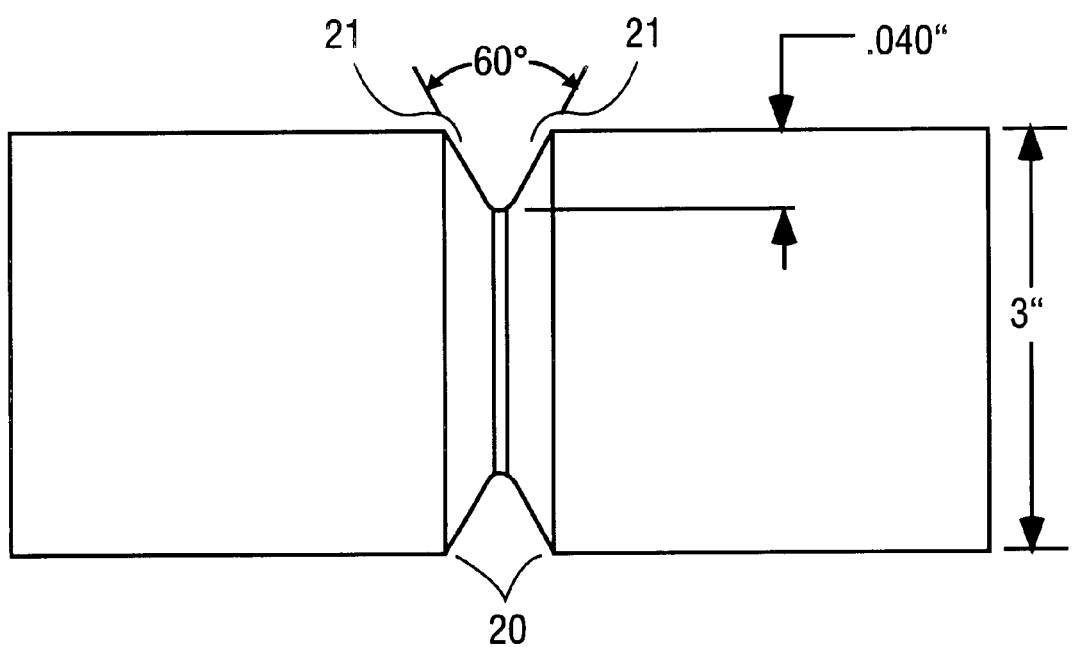
FIG. 7 shows a side view illustration of a primary roller.
Figure 8:
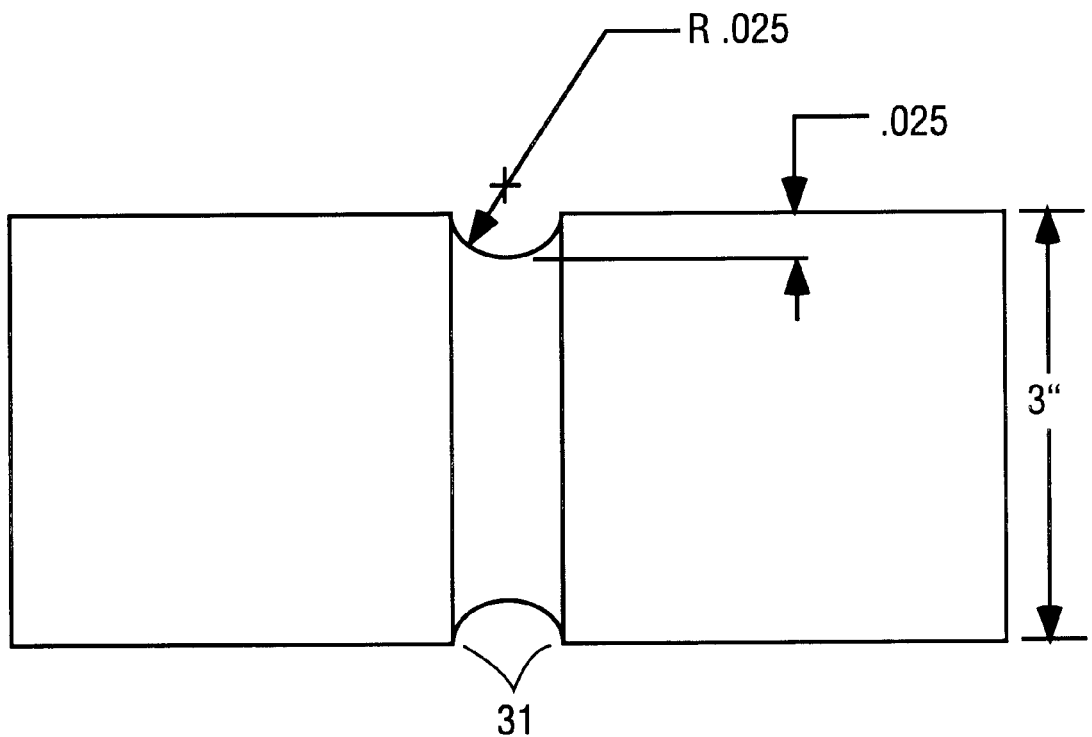
FIGS. 8, 9 and 10 show side view illustrations of stage rollers.
Figure 9:
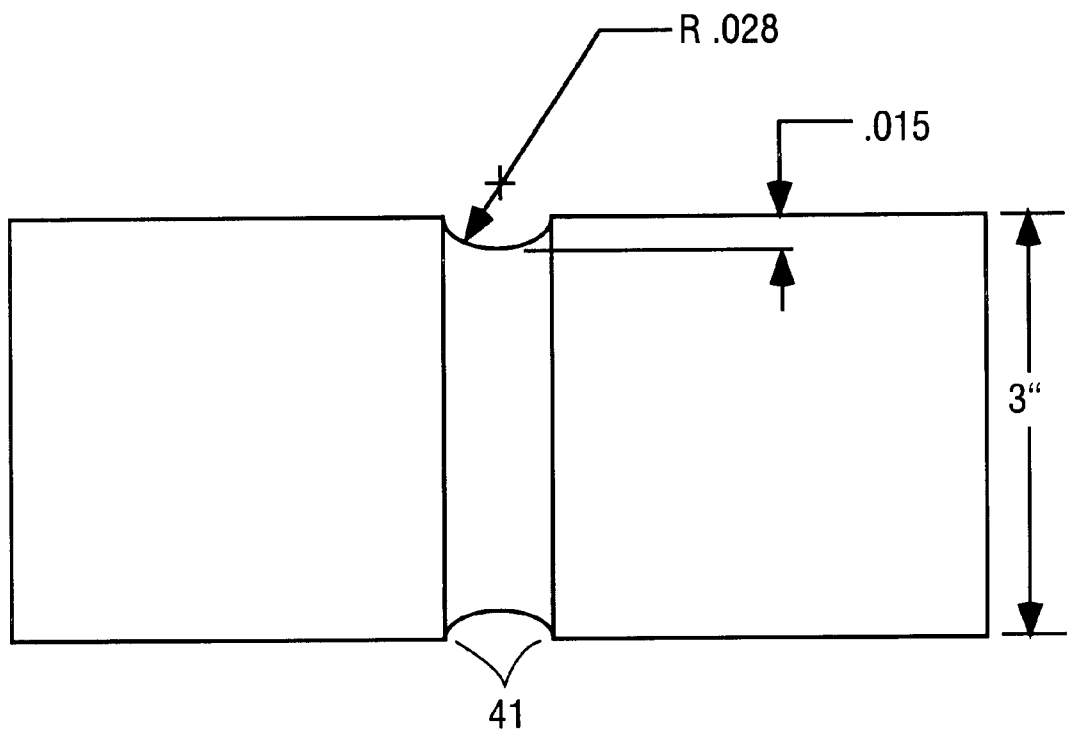
Figure 10:
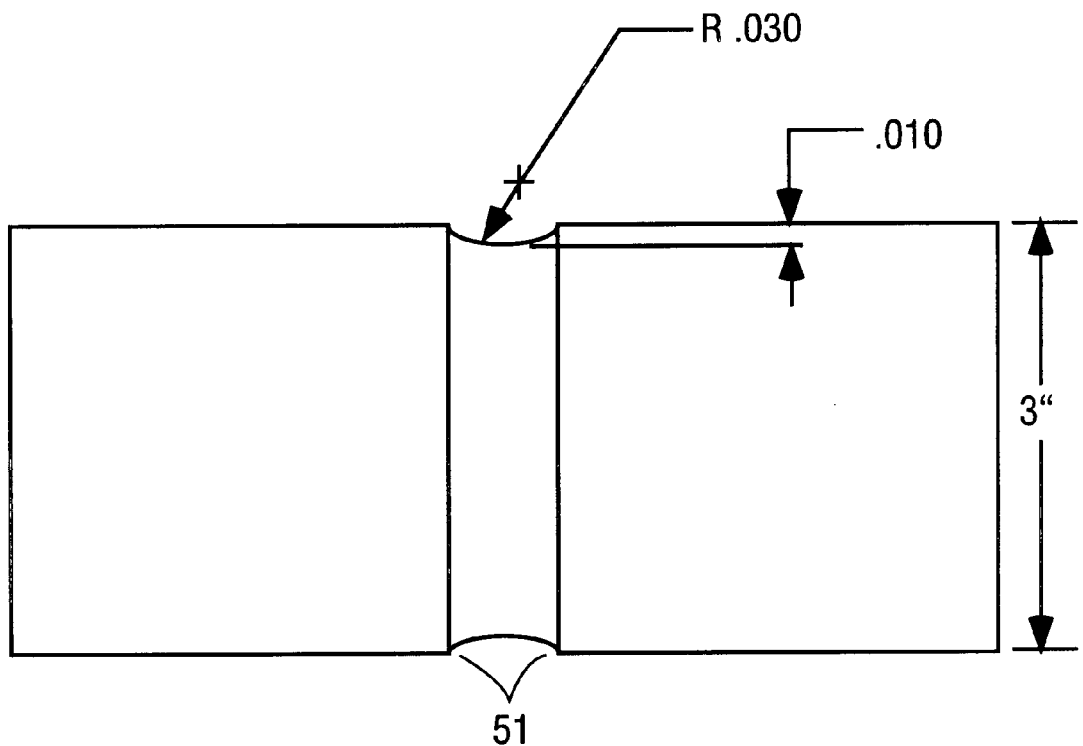

By means of example, the formation of a wire with a cross-section that is substantially triangular (see FIG. 6) but having a radiused base is detailed. In this instance, a radiused base of 0.030 inches and an arc of 60° is desired. A round wire of approximately 0.050 inch diameter is fed into the system. The primary roller such as primary roller 3, used for forming the desired wire, as shown in FIG. 7, has forming groove 20 which is used to form the angled sides 21 and 60° arc. In this instance, forming groove 20 is introduced in primary roller 3 to a depth of 0.040 inches. The stage one roller, as shown in FIG. 8, has a forming groove 31 formed in the shape of an arc having a radius to a focal point of 0.025 inches and a depth of 0.025 inches which is used to press the wire within the groove of set primary roller 3 and may begin forming the radiused base of the wire cross-section. The stage two roller, as shown with dimensions in FIG. 9, has a forming groove 41 formed in the shape of an arc (having a radius to focal point of 0.028 inches and a depth of 0.015 inches) which is used to press the wire deeper into the groove of the primary roller 3 and further from the radiused base of the wire cross-section. The stage three roller, as shown with dimensions in FIG. 10, has a forming groove 51 formed in the shape of an arc (having a radius to a focal point of 0.030 inches and a depth of 0.010 inches) which is used to press the wire to its final position in the primary roller 3, and to form the final radius on the base of the wire cross-section.

The number of progressive rollers which may be used according to the process of this invention is limited only by the diameter of the rollers and the ability to place these proximate to one another so as to eliminate the free space wherein proper wire orientation may be lost. In the embodiment previously described where a primary drive roller such as primary roller 3 is used, more than three rollers may be accommodated along the surface area of the primary roller circumference. Thus, upwards of five rollers can be oriented about the primary roller circumference.

Figure 4:
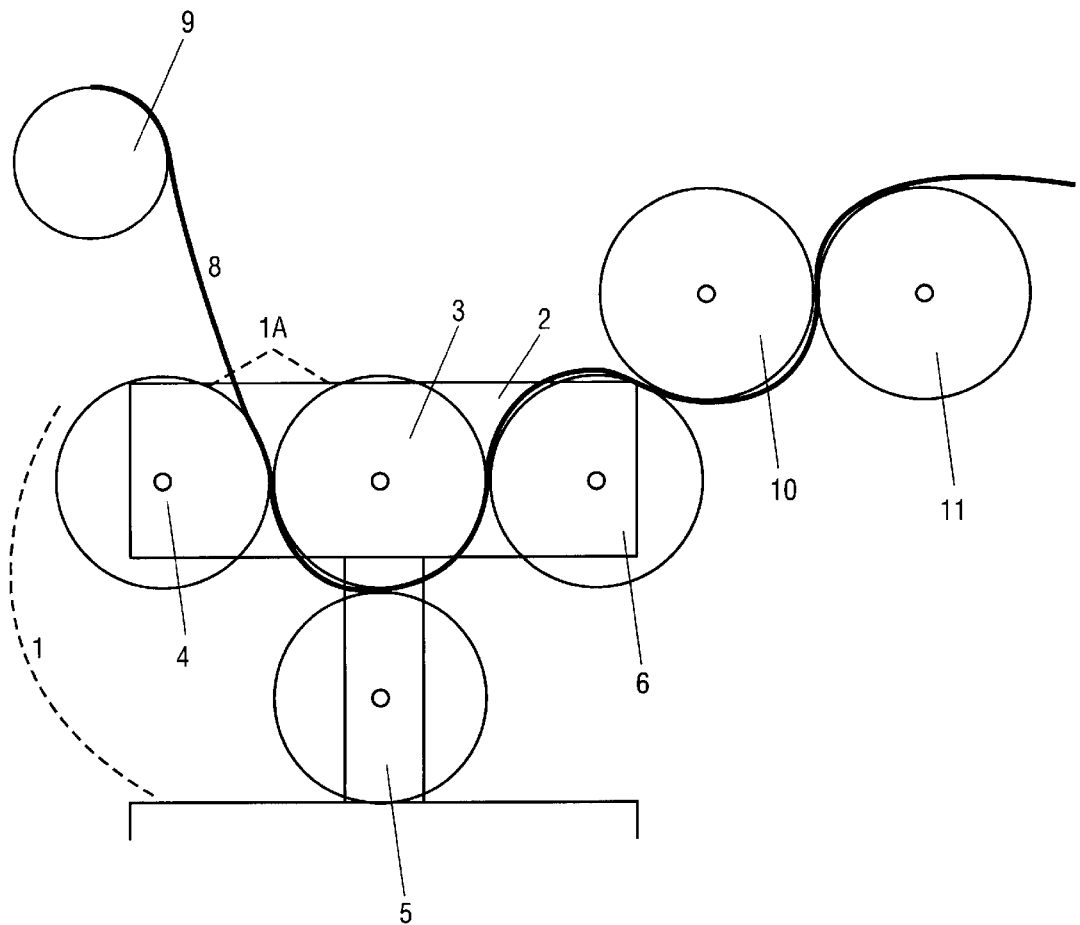
FIG. 4 illustrates the wire forming method according to an alternative embodiment of the invention.
Figure 5:
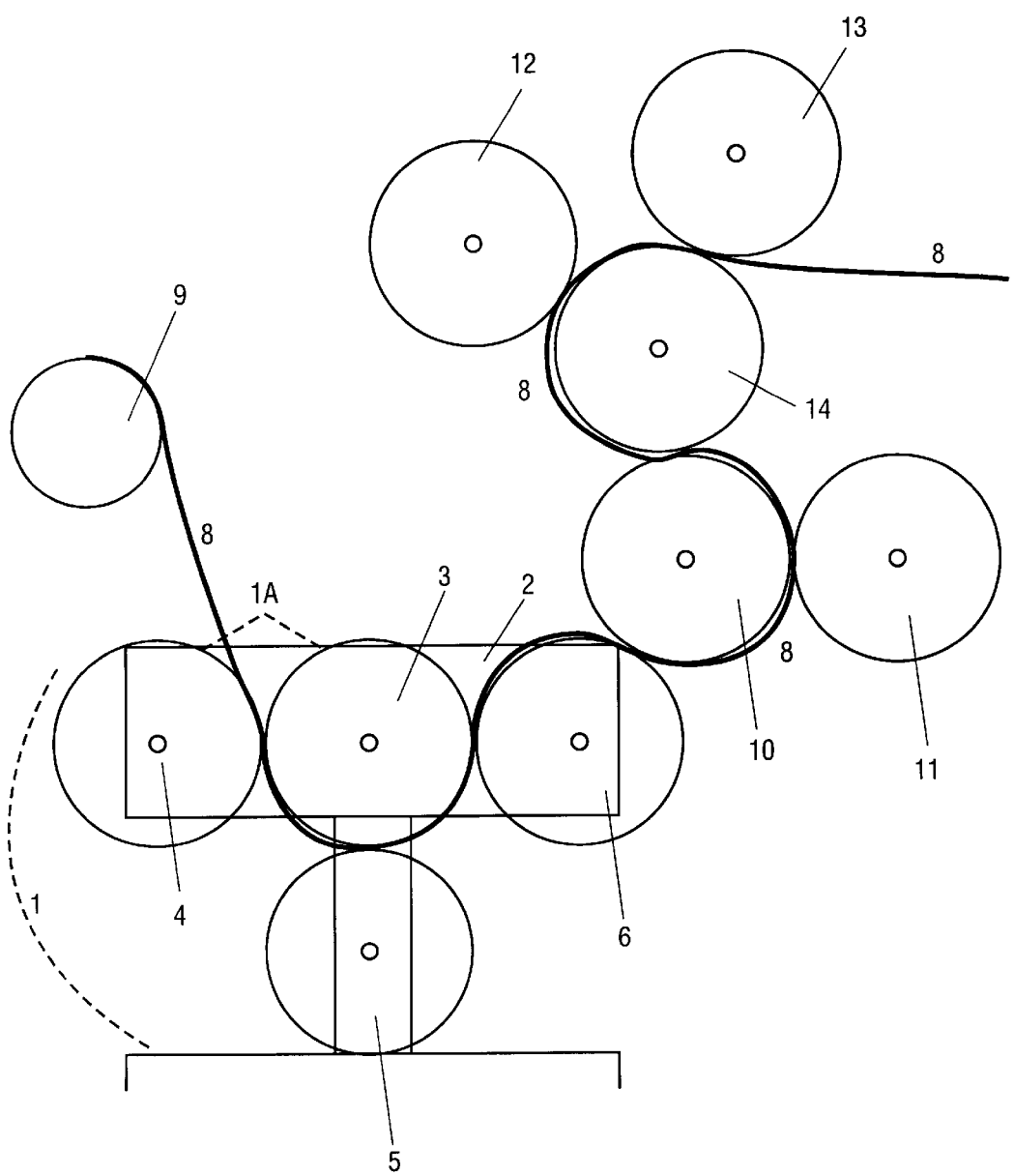
FIG. 5 illustrates the wire forming method according to an alternative embodiment of the invention.

Further embodiments may include multiple "primary rollers" arranged in alternative patterns. Thus, the wire may be further processed by adding additional rollers proximate, though not engaging, the primary roller. In FIG. 4 and FIG. 5, for example, the placement of the additional rollers 11,12 and 13 prevent the wire from being freely suspended between stages where the wire may lose its orientation. In the embodiment of FIG. 4, secondary roller 10, having forming groove (not pictured) may be employed in a fashion analogous to the use of the primary roller 3 in FIG. 3. The embodiment of FIG. 5 may be utilized, in one example, if additional forming stages are required and the surface area of primary roller 3 cannot accommodate the rollers intended for multiple stages or if additional wire forming to introduce alternate shapes by adding separate forming grooves on the additional rollers. This embodiment features tertiary roller 14 with forming groove (not pictured) contacting additional stage rollers 12 and 13 in a fashion analogous to the use of primary roller 3 in FIG. 3.

Use of a drive system in powering rotation in the various embodiments will depend upon the wire forming objectives. In some situations, for example, depending on the wire material and cross-section design, the drive system may power just the primary roller, while the stage rollers are free rotating, counter to the rotation of the driven primary roller, and not coupled to the drive train. In other situations, for example, the drive system may power just the last stage roller, which pulls the wire through the entire system. In some situations, for instance, the drive system may need to power all the rollers, and may rotate the stage rollers at different speeds. For example, each progressive stage roller may rotate faster than the stage roller preceding it. In other instances, the drive system may also need to rotate the primary, secondary and/or tertiary rollers at different speeds. The drive system may be configured in ways known in the art, including a drive train.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A process of forming a wire having a desired cross-sectional geometry comprising the steps of:

rotating a primary roller, the primary roller having a circumferential forming groove configured to receive a wire to be formed;

counter-rotating a first stage roller having a circumferential forming groove configured to receive a wire to be formed, the first stage roller engaging the primary roller at a first contact point;

counter-rotating a second stage roller having a circumferential forming groove configured to receive a wire to be formed, the second stage roller engaging the primary roller at a second contact point;

counter-rotating a third stage roller having a circumferential forming groove configured to receive a wire to be formed, the third stage roller engaging the primary roller at a third contact point;

running a pre-determined length of wire into the forming groove of the primary roller;

compressing the wire within the first stage roller forming groove at the first contact point;

compressing the wire within the second stage roller forming groove at the second contact point;

compressing the wire within the third stage roller forming groove at the third contact point;

having the primary roller, the first stage roller, the second stage roller and the third stage roller simultaneously maintaining contact with the wire without the wire being freely suspended between these rollers; and providing at least one drive train for rotational motion coupled to at least one of the primary roller, the first stage roller, the second stage roller and the third stage roller.

2. The process of claim 1, further comprising:

counter-rotating a fourth stage roller having a circumferential forming groove configured to receive a wire to be formed, the fourth stage roller engaging the primary roller at a fourth contact point;

compressing the wire within the fourth stage roller forming groove at the fourth contact point; and having the primary roller, the first stage roller, the second stage roller, the third stage roller and the fourth stage roller simultaneously maintaining contact with the wire without the wire being freely suspended between these rollers.

3. The process of claim 2, wherein at least one drive train is coupled to at least one of the primary roller, the first stage roller, the second stage roller, the third stage roller and the fourth stage roller.

4. The process of claim 2, further comprising:

counter-rotating a fifth stage roller having a circumferential forming groove configured to receive a wire to be formed, the fifth stage roller engaging the primary roller at a fifth contact point;

compressing the wire within the fifth stage roller forming groove at the fifth contact point; and having the primary roller, the first stage roller, the second stage roller, the third stage roller, the fourth stage roller and the fifth stage roller simultaneously maintaining contact with the wire without the wire being freely suspended between these rollers.

5. The process of claim 4, wherein at least one drive train is coupled to at least one of the primary roller, the first stage roller, the second stage roller, the third stage roller, the fourth stage roller and the fifth stage roller.

6. A process comprising:

rotating a primary roller having a circumferential forming groove configured to receive a wire to be formed;

providing a first stage roller having a circumferential forming groove configured to receive a wire to be formed engaging the primary roller at a first contact point;

providing a second stage roller having a circumferential forming groove configured to receive a wire to be formed engaging the primary roller at a second contact point;

running a pre-determined length of wire into the forming groove of the primary roller;

compressing the wire within the first stage roller forming groove at the first contact point;

compressing the wire within the second stage roller forming groove at the second contact point; and having the primary roller, the first stage roller and the second stage roller simultaneously maintaining contact with the wire without the wire being freely suspended between these rollers.

7. The process of claim 6, wherein the position of the first and second stage rollers are adjustable with respect to the primary roller to regulate the compressive force exerted at the first and second contact points.

8. The process of claim 6, further comprising:

providing a third stage roller having a circumferential forming groove engaging the primary roller at a third contact point;

compressing the wire within the third stage roller forming groove at the third contact point; and having the primary roller, the first stage roller, the second stage roller and the third stage roller simultaneously maintaining contact with the wire without the wire being freely suspended between these rollers.

9. The process of claim 6, wherein the position of the third stage rollers is adjustable with respect to the primary roller to regulate the compressive force exerted at the third contact point.

10. The process of claim 6, further comprising:

rotating a secondary roller having a circumferential forming groove configured to receive a wire to be formed, the secondary roller being in close proximate with the primary roller;

providing a secondary stage roller having a circumferential forming groove configured to receive a wire to be formed engaging the secondary roller at a first contact point;

running the wire out of the primary roller circumferential forming groove;

running the wire into the secondary roller circumferential forming groove;

compressing the wire within the secondary stage roller forming groove at the secondary roller first contact point; and having the third stage roller, the secondary roller and the secondary stage roller simultaneously maintaining contact with the wire without the wire being freely suspended between these rollers.

11. The process of claim 6, wherein the position of the secondary stage roller is adjustable with respect to the secondary roller to regulate the compressive force exerted at the secondary roller first contact point.

12. The process of claim 10, wherein the secondary stage roller is a first secondary stage roller and the process further comprises:

providing a second secondary stage roller having a circumferential forming groove configured to receive a wire to be formed engaging the secondary roller at a second contact point;

compressing the wire within the second secondary stage roller forming groove at the secondary roller second contact point; and having the third stage roller, the secondary roller, the first secondary stage roller and the second secondary stage roller simultaneously maintaining contact with the wire without the wire being freely suspended between these rollers.

13. The process of claim 10, further comprising:

rotating a tertiary roller having a circumferential forming groove configured to receive a wire to be formed, the tertiary roller being in close proximate with the secondary roller;

providing a tertiary stage roller having a circumferential forming groove configured to receive a wire to be formed engaging the secondary roller at a first contact point;

running the wire out of the secondary roller circumferential forming groove;

running the wire into the tertiary roller circumferential forming groove;

compressing the wire within the tertiary stage roller forming groove at the tertiary roller first contact point; and having the second secondary stage roller, the tertiary roller and the tertiary stage roller simultaneously maintaining contact with the wire without the wire being freely suspended between these rollers.

14. The process of claim 13, wherein the position of the tertiary stage roller is adjustable with respect to the tertiary roller to regulate the compressive force exerted at the tertiary roller first contact point.

15. The process of claim 13, wherein the tertiary stage roller is a first tertiary stage roller and the process further comprises:

providing a second tertiary stage roller having a circumferential forming groove configured to receive a wire to be formed engaging the tertiary roller at a second contact point;

compressing the wire within the second tertiary stage roller forming groove at the secondary roller second contact point; and having the second secondary stage roller, the tertiary roller, the first tertiary stage roller and the second tertiary stage holder simultaneously maintaining contact with the wire without the wire being freely suspended between these rollers.

16. The process of claim 15, wherein at least one drive train rotates at least one of the primary roller, secondary roller and tertiary roller.

17. The process of claim 15, wherein at least one drive train is coupled to at least one of the stage rollers.

18. An apparatus comprising:

a frame;

a primary roller having a circumferential forming groove configured to receive a wire to be formed, the primary roller coupled to the frame;

a first stage roller having a circumferential forming groove configured to receive a wire to be formed engaging the primary roller at a first contact point in a manner to keep the wire in contact with at least one roller at anytime, the first stage roller being coupled to the frame;

a second stage roller having a circumferential forming groove configured to receive a wire to be formed engaging the primary roller at a second contact point in a manner to keep the wire in contact with at least one roller at anytime, the second stage roller having coupled to the frame.

19. The apparatus of claim 18, further comprising:

a drive train coupled to the primary roller.

20. The apparatus of claim 18, further comprising:

at least one drive train coupled to one of the first stage roller and the second stage roller.

21. The apparatus of claim 18, further comprising:

a third stage roller having a circumferential forming groove configured to receive a wire to be formed engaging the primary roller at a second contact point the third stage roller coupled to the frame.

22. An apparatus comprising:

a "T" shaped frame having a center, a first arm, a second arm and a base;

a primary roller having circumferential forming groove configured to receive a wire to be formed;

a first stage roller having a circumferential forming groove configured to receive a wire to be formed engaging the primary roller at a first contact point;

a second stage roller having a circumferential forming groove configured to receive a wire to be formed engaging the primary roller at a second contact point;

a third stage roller having a circumferential forming groove configured to receive a wire to be formed engaging the primary roller at a third contact point; and the primary roller coupled to the center of the frame, the first stage roller coupled to the first arm of the frame, the third stage roller coupled to the second arm of the frame and the second stage roller coupled to the base of the frame.

23. The apparatus of claim 21, further comprising:

at least one drive train coupled to one of the first stage roller, the second stage roller and the third stage roller.

24. The apparatus of claim 22, further comprising:

a drive train coupled to the primary roller.

25. The apparatus of claim 22, further comprising:

at least one drive train coupled to one of the first stage roller and the second stage roller.

26. The apparatus of claim 22, further comprising:

at least one drive train coupled to one of the first stage roller, the second stage roller and the third stage roller.

* * * * *

UNITED STATES PATENT AND TRADEMARK OFFICE
CERTIFICATE OF CORRECTION

PATENT NO.    : 6,237,386 B1
DATED         : May 29, 2001
INVENTOR(S)   : Schmidt It is certified that error appears in the above-identified patent and that said Letters Patent is hereby corrected as shown below:

<u>Column 8,</u>
Line 11, delete "having" and insert -- being --.
Line 22, delete "second" and insert -- third --.
Line 22, delete "contact point" and insert -- contact point, --.

Signed and Sealed this

Twenty-eighth Day of May, 2002

Attest:

JAMES E. ROGAN
*Attesting Officer*   *Director of the United States Patent and Trademark Office*